United States Patent [19]

Wiedmer

[11] Patent Number: 4,783,475

[45] Date of Patent: Nov. 8, 1988

[54] COMPOSITIONS CONTAINING α-(1-CYCLOPROPYLETHYL)-α-(P-CHLOROPHENYL)-1H-1,2,4-TRIAZOLE-1-ETHANOL AND A GUANIDINE COMPOUND AND FUNGICIDAL USE THEREOF

[75] Inventor: Hans Wiedmer, Therwil, Switzerland

[73] Assignee: Sandoz Ltd., Basel, Switzerland

[21] Appl. No.: 74,797

[22] Filed: Jul. 17, 1987

[30] Foreign Application Priority Data

Jul. 21, 1986 [GB] United Kingdom ............... 8617780

[51] Int. Cl.$^4$ .................... A01N 37/52; A01N 43/64
[52] U.S. Cl. ...................................... 514/383; 514/636
[58] Field of Search .................... 514/383, 634, 636

[56] References Cited

U.S. PATENT DOCUMENTS

| | | | |
|---|---|---|---|
| 3,499,927 | 3/1970 | Badcock et al. | 564/236 |
| 3,639,631 | 2/1972 | Badcock et al. | 514/636 |
| 4,664,696 | 5/1987 | Schaub | 514/383 |

FOREIGN PATENT DOCUMENTS

| | | | |
|---|---|---|---|
| 0155509 | 9/1985 | European Pat. Off. | 514/634 |
| 2064520 | 6/1981 | United Kingdom | 514/383 |

Primary Examiner—Allen J. Robinson
Attorney, Agent, or Firm—Gerald D. Sharkin; Richard E. Vila

[57] ABSTRACT

The invention provides a method of combatting fungal diseases with the aid of
(a) the compound of formula I

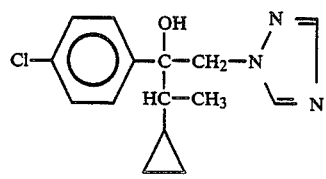

and
(b) the compound of formula II

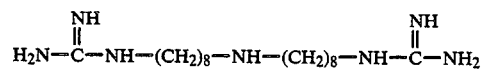

and fungicidal compositions comprising said compounds.

12 Claims, No Drawings

COMPOSITIONS CONTAINING α-(1-CYCLOPROPYLETHYL)-α-(P-CHLOROPHENYL)-1H-1,2,4-TRIAZOLE-1-ETHANOL AND A GUANIDINE COMPOUND AND FUNGICIDAL USE THEREOF

The present invention relates to fungicides.

The invention provides a method of combatting fungal diseases in plants, with the aid of
(a) the compound of formula I

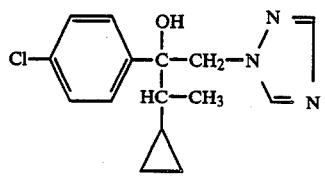

and
(b) the guanidine compound of formula II

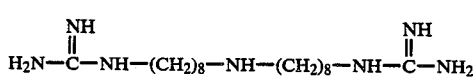

The compounds of formula I and II may be in free base form or in fungicidally acceptable acid addition salt form. Said salt forms exhibit the same order of activity as the free base forms.

The compound of the formula I (which may be named α-(1-cyclopropylethyl)-α-(p-chlorophenyl)-1H-1,2,4-triazole-1-ethanol) is a known fungicide, effective in the combatting of fungi in crops such as cereals including rice, especially in wheat and barley; it has excellent activity against rusts (such as Puccinia spp.), good activity against powdery mildews (such as Erysiphe), and interesting suppressive activities against Septoria, Pyrenophora, Rhynchosporium and Pseudocercosporella.

The compound of formula I is usually employed in free base form.

The compound of formula II is known to be effective against plant fungi and used i.a. for cereal seed treatment and, in foliar spray form, against phytopathogenic fungi such as *Pyricularia oryzae* (in rice) and Septoria spp. (in wheat). The triacetate salt of the compound of formula II is known under the common name iminoctadine. Said triacetate salt is also an active ingredient of the plant fungicidal mixture known under the common name guazatine.

It has now been found that the use of the compound of formula I in combination with the compound of formula II (combination of the invention) is surprisingly effective in the combatting of various fungi. Thus, more than additive effect is i.a. observed in tests against Erysiphe (barley, wheat), Pyrenophora, Septoria and Pseudocercosporella.

Though the efficacy of the combination of the invention will depend on the particular fungi (disease) to be combatted, the crop involved, the desired treatment (foliar, soil or seed treatment), the weight ratio of the compound of formula I: compound of formula II and other parameters, the test results indicate that the combination of the invention is surprisingly effective against powdery mildews, foot diseases and ear diseases, and is accordingly particularly indicated for use in crops sensitive to such diseases. Such crops comprise cereals (including including herein—by definition—rice) and vines, particularly wheat, barley and rice, more particularly wheat and barlry.

Accordingly, the invention provides an improved method of combatting fungal diseases in plants, especially in cereals, which comprises, applying to the plants, in admixture or separately, the compounds of the formulae I and II in free base form or agriculturally acceptable salt form, in a fungicidally effective aggregate amount.

For control of air-borne fungi, the compounds are conveniently employed as foliar sprays.

Where the compound of formula II is employed in triacetate form, i.e. as iminoctadine, satisfactory results may, in general, be obtained when applying 50 to 100 g, particularly 60 to 80 g of the compound of formula I and 100 to 500 g, particularly 200 to 400 g, e.g. 250 of iminoctadine per hectare of crop locus.

Suitable weight ratios of the compound of formula I:iminoctadine lie in the range of 4:1 to 1:8, particularly of 3:1 to 1:6, more particularly of 3:1 to 1:4, most particularly of 2:1 to 1:4. Thus the experimental data given hereinafter show for example synergism for several crop/fungus diseases for the weight ratios 2:1, 1:1 and 1:2 (i.e. for the range 2:1 to 1:2).

Where the compound of formula II is in base form, or in a salt form other than the triacetate form it will in general be appropriate to adapt the amount of compound of formula II to be employed in the method and compositions of the invention by a factor equivalent to the molecular weight ratios of the base form or particular salt form to that of the triacetate salt form.

A similar consideration applies also to the compound of formula I when employed in salt form.

Thus, for example, the amount of the compound of formula II to be applied when in base form would be a factor of about 0.66 lower, and be in the range of from 66 to 330 g, particularly from 132 to 264, e.g. 165.

Similar adaptation is appropriate with respect to the weight ratios; where, for example, both compounds are applied in base form the weight ratio of the compound of formula I:compound of formula II are conveniently in the range of 6:1 to 1:5.3, particularly of 4.5:1 to 1:2.6, moreparticularly of from 4.5:1 to 1:2.6, most particularly of from 3:1 to 1:2.6, e.g. of from 3:1 to 1:1.3.

The invention also provides fungicidal compositions comprising the compounds of formula I and II, preferably in a weight ratio within the range specified herein above.

Such compositions of the invention may be formulated in any conventional form, for example in the form of a twin packet, or of an emulsifiable concentrate, wettable powder or water dispersible granule. Such compositions may be produced in conventional manner, e.g. by mixing the compounds of formula I and II with appropriate adjuvants such as diluents and optionally other formulating ingredients such as surfactants.

The term diluent as used herein means any liquid or solid agriculturally acceptable material—including carriers—which may be added to the active constituents to bring them in an application or commercial form, respectively, to a usable or desirable strength of activity. It can for example be talc, kaolin, diatomaceous earth, mineral oil, or water.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, from 0 to 20% agriculturally acceptable surfactant and 10 to 99.99% of diluent, the active agent consisting of the compounds of formula I and II and optionally other active agents.

In addition to the usual diluents and surfactants, the compositions of the invention may comprise further additives with special purposes, such as anti-foaming agents. Moreover, further fungicides with similar or complementary fungicidal activity, e.g. tridemorph, fenpropimorph, fenpropidin, pyrazophos, prochloraz, mancozeb, sulphur and carbendazim, or other beneficially-acting materials, such as insecticides may be present in the formulation.

Concrete forms of compositions in general contain between about 2 and 80%, preferably between about 5 and 70% by weight of active agent. Application forms of formulation may for example contain from 0.01 to 45% by weight.

The invention is illustrated by the following examples, wherein parts and percentages are by weight.

FORMULATION EXAMPLE

| Wettable Powder | Parts |
| --- | --- |
| Compound of formula I | 40 |
| Iminoctadine | 40 |
| Na dodecylsulphate | 1 |
| Na lignin sulphonate | 5 |
| Kaolin | 14 |

The compounds are mixed and milled until the mean particle size is about 5 microns.

GREENHOUSE TEST

In vivo employing Erysiphe graminis fs. tritici on wheat

Wheat is cultivated in a mixture of peat and sand in plastic pots of 6 cm diameter for x days. The plants are sprayed with aqueous spray liquors containing the compound of formula I, iminoctadine or mixtures thereof (hereinafter a.i.) in various concentrations. The treatment comprises foliar spraying to near run-off. After drying, the plants are inoculated by dusting them with freshly collected conidia and are then incubated in an incubation chamber at 60-80% relative humitiy, 16 hours daylight and 20°-25° C. The efficacy of the a.i. is determined by the degree of fungal attack with that on untreated, similarly inoculated check plants, and is expressed in % control for a given test concentration. Each a.i. is tested in different concentrations. This allows for the determination of the EC 90 exp. value, i.e. the concentration of each a.i. allowing 90% disease control. The experimental result (EC 90 exp.) for a given weight ratio of the compounds of formula I and iminoctadine is compared with the corresponding EC 90 theor. value, i.e. the concentration of that particular mixture allowing 90% disease control calculated according to Wadley $$EC_{(ab)}90 \text{ theor.} = \frac{a+b}{\frac{a}{EC_{(a)}90 \text{ exp.}} + \frac{b}{EC_{(b)}90 \text{ exp.}}}$$

wherein a and b are the weight ratios of the compounds of formula I and iminoctadine resp. and the indexes (I), (II) and (I+II) refer to the EC 90 values of the compound of formula I, iminoctadine and the a:b mixture of the compound of formula I with iminoctadine resp. In the case of synergism EC(I+II)90 theor. is greater than EC(I+II)90 exp., or the level or interaction, i.e. the synergy factor (SF)

$$SF = \frac{EC_{(I+II)}90 \text{ theor.}}{EC_{(I+II)}90 \text{ exp.}} > 1$$

Analogous tests are run with
Erys. gram. f. sp. hordei on barley
Pyrenophora on barley
Septoria on wheat, and
Pseudocercosporella on wheat The results in which EC 90 values are expressed in ppm or mg/liter are as follows:

|  |  | EC90 exp. | EC90 theor. | SF |
| --- | --- | --- | --- | --- |
| 1. Erysiphe/barley |  |  |  |  |
| Compound of formula I |  | 3.1 |  |  |
| Iminoctadine |  | 37.0 |  |  |
| Weight ratio of compounds of | 1.0:0.5 | 2.9 | 4.46 | 1.5 |
| formula I:iminoctadine | 1.0:1.0 | 2.8 | 5.72 | 2.0 |
|  | 1.0:2.0 | 3.2 | 7.97 | 2.5 |
| 2. Erysiphe/wheat |  |  |  |  |
| Compound of formula I |  | 2.5 |  |  |
| Iminoctadine |  | 35.0 |  |  |
| Weight ratio of compounds of | 1.0:0.5 | 2.9 | 3.62 | 1.3 |
| formula I:iminoctadine | 1.0:1.0 | 2.5 | 4.67 | 1.9 |
|  | 1.0:2.0 | 2.8 | 6.56 | 2.3 |
| 3. Pyrenophora/barley |  |  |  |  |
| Compound of formula I |  | 11.00 |  |  |
| Iminoctadine |  | 18.00 |  |  |
| Weight ratio of compounds of | 1.0:0.5 | 8.5 | 12.64 | 1.5 |
| formula I:iminoctadine | 1.0:1.0 | 6.3 | 13.66 | 2.2 |
|  | 1.0:2.0 | 5.8 | 14.85 | 2.6 |
| 4. Septoria/wheat |  |  |  |  |
| Compound of formula I |  | 10.0 |  |  |
| Iminoctadine |  | 24.0 |  |  |
| Weight ratio of compounds of | 1.0:0.5 | 3.2 | 12.41 | 3.9 |
| formula I:iminoctadine | 1.0:1.0 | 6.0 | 14.12 | 2.4 |
|  | 1.0:2.0 | 7.5 | 16.36 | 2.2 |
| 5. Pseupocercosporella/wheat |  |  |  |  |
| Compound of formula I |  | 32.0 |  |  |
| Iminoctadine |  | 29.0 |  |  |
| Weight ratio of compounds of | 1.0:0.5 | 8.5 | 30.93 | 3.6 |
| formula I:iminoctadine | 1.0:1.0 | 9.0 | 30.43 | 3.4 |
|  | 1.0:2.0 | 11.0 | 29.94 | 2.7 |

I claim:

1. A method of combatting a fungus disease selected from the group consisting of Erysiphe, Pyrenophora, Septoria and Pseudocercosporella in crop plants sensitive to such a fungus comprising applying to the plants in a crop locus, in admixture or separately, a fungicidal effective total amount of (a) the compound of the formula I

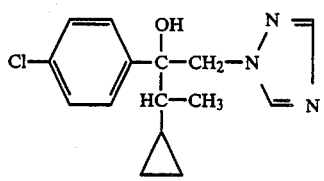

and (b) the compound of the formula II

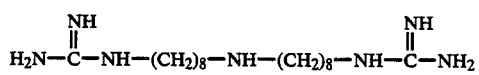

said compounds of the formulae I and II independently being in free base or acid addition salt form and the weight ratio of the compound of the formula I to the compound of the formula II in such application being in the range equivalent to 2:1 to 1:2 on the basis of the compound of the formula I in free base form and the compound of the formula II in triacetate acid addition salt form.

2. The method of claim 1, which comprises applying per hectare of crop locus from 50 to 100 g of the compound of formula I in base form or an equivalent amount of said compound in acid addition salt form, and from 100 to 500 g of the triacetate of the compound of formula II or an equivalent amount of said compound in another acid addition salt form or in base form.

3. The method of claim 1, wherein the crop is a cereal or vine crop.

4. The method of claim 3, in which Erysiphe graminis, Pyrenophora, Septoria or Pseudocercosporella spp is combatted in a cereal crop.

5. The method of claim 2 in which the compound of the formula I is applied in free base form and the compound of the formula II is applied in triacetate acid addition salt form.

6. The method of claim 5, wherein the applied amount per hectare of crop locus compound of formula I in base form is from 60 to 80 g and that of the compound of formula II in triacetate form is from 200 to 400 g.

7. The method of claim 3 in which Erysiphe is combatted in barley or wheat.

8. The method of claim 3 in which Pyrenophora is combatted in barley.

9. The method of claim 3 in which Septoria is combatted in wheat.

10. The method of claim 3 in which Pseupocercosporella is combatted in wheat.

11. A fungicidal composition comprising an agriculturally acceptable diluent and a fungicidally effective total amount of (a) the compound of the formula I

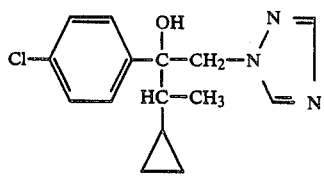

and (b) the compound of the formula II

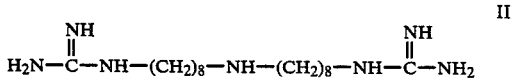

said compounds of the formula I and II independently being in free base or acid addition salt form and the weight ratio of the compound of the formula I to the compound of the formula II being in the range equivalent to 2:1 to 1:2 on the basis of the compound of the formula I in free base form and the compound of the formula II in triacetate acid addition salt form.

12. The composition of claim 11 in which the compound of the formula I is in free base form and the compound of the formula II is in triacetate acid addition salt form.

* * * * *